(12) United States Patent
Hosseini

(10) Patent No.: US 11,779,469 B2
(45) Date of Patent: Oct. 10, 2023

(54) ORTHOPEDIC IMPACTOR ATTACHMENT

(71) Applicant: Miramin Hosseini, Irvine, CA (US)

(72) Inventor: Miramin Hosseini, Irvine, CA (US)

( * ) Notice: Subject to any disclaimer, the term of this patent is extended or adjusted under 35 U.S.C. 154(b) by 108 days.

(21) Appl. No.: 17/528,815

(22) Filed: Nov. 17, 2021

(65) Prior Publication Data

US 2022/0370210 A1     Nov. 24, 2022

Related U.S. Application Data

(60) Provisional application No. 63/191,568, filed on May 21, 2021.

(51) Int. Cl.
    *A61F 2/46*         (2006.01)
    *A61B 17/92*       (2006.01)

(52) U.S. Cl.
    CPC ............ *A61F 2/4603* (2013.01); *A61B 17/92* (2013.01); *A61F 2002/4627* (2013.01)

(58) Field of Classification Search
    CPC ........... A61F 2/4603; A61F 2002/4627; A61B 17/92; B25D 16/17; B25D 16/00; B25D 16/003; B25D 16/006; B25D 17/00; B25D 17/005; B25D 17/02; B25D 17/04; B25D 17/043; B25D 17/046; B25D 17/06; B25D 17/08; B25D 17/082; B25D 17/084; B25D 17/086; B25D 17/088; B25D 17/11; B25D 17/12; B25D 17/20; B25D 17/22; B25D 17/24; B25D 17/245; B25D 17/26; B25D 17/265; B25D 17/28; B25D 17/30; B25D 17/32; B25D 2216/0023

USPC .......................................................... 606/99
See application file for complete search history.

(56) References Cited

U.S. PATENT DOCUMENTS

| | | | | |
|---|---|---|---|---|
| 2,965,258 A | * | 12/1960 | Wilson ................... | B21J 15/043 72/450 |
| 3,807,242 A | * | 4/1974 | Stone ...................... | F16H 23/10 74/56 |
| 3,822,595 A | * | 7/1974 | Elflein ................... | B21J 15/043 29/243.526 |
| 3,823,473 A | * | 7/1974 | Hoffman ................ | B23D 51/10 83/750 |
| 5,511,912 A | * | 4/1996 | Ellerbrock ............. | B23D 51/16 74/56 |
| 2005/0199117 A1 | * | 9/2005 | Quinn .................... | B23D 51/10 83/698.11 |

(Continued)

*Primary Examiner* — Jessica Weiss
(74) *Attorney, Agent, or Firm* — Brennan, Manna & Diamond, LLC

(57) ABSTRACT

The present invention relates to a portable medical drill impact attachment device. The device can be used for improving the accuracy and reliability of orthopedic surgeries and procedures by obviating a manual device such as a hammer for creating an impact. The attachment device is used for creating impact forces that can be transferred onto a bone, disc, joint, etc. The device features a housing that includes a rotary motion transformer and an impact mechanism assembly. The attachment transforms the rotational motion of a drill into reciprocal motion, and also enables a user to adjust and control the frequency and energy of the impact. An impactor tool can be detachably-attached to a quick-change tool gripper for providing an impact on a bone, disc or joint of a patient without applying any manual force.

18 Claims, 6 Drawing Sheets

(56) References Cited

U.S. PATENT DOCUMENTS

| | | | | |
|---|---|---|---|---|
| 2007/0141529 A1* | 6/2007 | Bouneff | ................... | A61C 1/07 |
| | | | | 433/118 |
| 2011/0255927 A1* | 10/2011 | Boudreau | .............. | B23D 51/16 |
| | | | | 279/144 |
| 2017/0042692 A1* | 2/2017 | Stewart | ................... | A61F 2/442 |

* cited by examiner

ORTHOPEDIC IMPACTOR ATTACHMENT

CROSS-REFERENCE TO RELATED APPLICATION

The present application claims priority to, and the benefit of, U.S. Provisional Application No. 63/191,568, which was filed on May 21, 2021 and is incorporated herein by reference in its entirety.

FIELD OF THE INVENTION

The present invention relates generally to the field of orthopedic surgery tools used for impacting. More specifically, the present invention relates to a medical drill impact attachment for improving the accuracy and reliability of orthopedic surgeries and procedures. The attachment device is used for creating impact forces that can be transferred onto a bone, disc, joint, etc. The device is portable and includes a housing having a rotary motion transformer and an impact mechanism assembly. The attachment transforms the rotational motion of a drill into reciprocal motion, and also enables a user to adjust and control the frequency and energy of the impact. An impactor tool can be detachably-attached for providing an impact on a bone, disc or joint of a patient without applying any manual force. Accordingly, the present disclosure makes specific reference thereto. Nonetheless, it is to be appreciated that aspects of the present invention are also equally applicable to other like applications, devices and methods of manufacture.

BACKGROUND

By way of background, orthopedic surgeries are performed on hard bones, bone fragments and joints. These surgeries require a surgeon to use specific external tools on the disks, bones and joints of a patient with precision. As an example, for implanting an artificial joint or replacing a bone fragment, an impact tool is required for creating a cavity in a bone or even to remove an existing bone or bone fragment. Various orthopedic prosthetic devices are used to replace diseased tissue of the patient, for example at a joint such as the knee, hip or shoulder. Currently, a manual device such as a hammer is used for creating an impact on a desired bone or bone fragment by a surgeon for performing orthopedic surgeries. Use of such manual devices and tools do not provide accurate impact, and are often tiring for the surgeon which decreases his or her performance, efficiency and efficacy.

In procedures that require creating a housing in a pelvic bone and placing an orthopedic cup, the manual devices are inefficient. Use of a manual hammer as an impactor does not allow the surgeon to house the cup efficiently and precisely, and can also lead to contamination to the patient. The manual hammer is a heavy tool that does not allow the surgeon to operate it smoothly and accurately, whereby the direction of impact can also become inaccurate while using the hammer.

Current tools for impacting and drilling do not include any means for the control of the penetration, and only the surgeon's manual skill is used to arrest the penetration and impact of the tool while performing the surgery. The manual manipulation of the tool can cause bone/soft tissue breakthrough which can cause unnecessary damage to the patient. Further, multiple external tools are typically required for cutting, shaping, fixating and dissecting bone for handling all types of orthopedic procedures.

Further, current impactor tools do not allow the surgeons to control and adjust the energy of the impact. This makes such devices less useful, as each bone requires different strength of impact for the orthopedic surgeries and procedures.

Therefore, there exists a long felt need in the art for an orthopedic surgery impact tool that enables orthopedic surgeries to be more accurate and reliable. There is also a long felt need in the art for an orthopedic surgery impact tool that can be easily used on any bone, disc, joint or more. Additionally, there is a long felt need in the art for an orthopedic surgery impact tool that eliminates the use of a manual hammer for creating an impact. Moreover, there is a long felt need in the art for an orthopedic surgery impact tool that enables users to adjust and control the frequency and energy of each impact. Furthermore, there is a long felt need in the art for an orthopedic surgery impact tool that is easy to carry and easy to use without tiring the surgeon. Finally, there is a long felt need in the art for an orthopedic surgery impact tool that improves the overall effectiveness of orthopedic surgeries and prevents further injury to the patient.

The subject matter disclosed and claimed herein, in one embodiment thereof, comprises an orthopedic impacting device that is configured to be used as a medical/surgical drill impact attachment for improving the accuracy and reliability of orthopedic surgeries and procedures. The orthopedic impacting device comprises a housing having a proximal end and a distal end. The device attaches to a medical drill using a drill bit positioned at the proximal end. Additionally, the housing includes a rotary motion-converting mechanism subassembly and an adjustable impacting mechanism subassembly. The rotary motion converting mechanism subassembly is configured to transform rotation motion provided by the medical drill into a reciprocating motion for creating impact forces and the adjustable impacting mechanism subassembly is configured for adjusting and controlling the frequency and energy of the impact using an adjustable switch. The orthopedic impacting device also includes a quick-change tool gripper positioned at the distal end that is configured to receive an impactor tool such as a broach, chisel or the like, for providing an impact force.

In this manner, the improved medical drill impact attachment of the present invention accomplishes all of the forgoing objectives and provides a relatively safe, convenient and lightweight orthopedic procedure device for accurate and effective orthopedic surgeries and procedures. The device provides impact forces onto a bone, disc, joint, etc., and can be used with any medical drill. The housing enables the components to be secured thereto and thus the device can be easily carried and used by a surgeon for performing various types of orthopedic procedures.

SUMMARY OF THE INVENTION

The following presents a simplified summary in order to provide a basic understanding of some aspects of the disclosed innovation. This summary is not an extensive overview, and it is not intended to identify key/critical elements or to delineate the scope thereof. Its sole purpose is to present some general concepts in a simplified form as a prelude to the more detailed description that is presented later.

The subject matter disclosed and claimed herein, in one embodiment thereof, comprises an orthopedic impacting device. The orthopedic impacting device is configured to be used as medical drill impact attachment for improving the accuracy and reliability of orthopedic surgeries and procedures. The orthopedic impacting device further comprises a housing having a proximal end and a distal end, the device attaches to a medical drill using a drill bit positioned at the proximal end, the housing includes a rotary motion-converting mechanism subassembly and an adjustable impacting mechanism subassembly. The rotary motion converting mechanism subassembly is configured to transform rotation motion provided by the medical drill into a reciprocating motion for creating impact forces and the adjustable impacting mechanism subassembly is configured for adjusting and controlling the frequency and energy of the impact using an adjustable switch. The orthopedic impacting device also includes a quick-change tool gripper positioned at the distal end that is configured to receive an impactor tool such as a broach, chisel, or the like, for providing an impact force.

In yet another embodiment, an orthopedic surgery impact attachment is disclosed. The orthopedic surgery impact attachment includes a rotary motion transformer subassembly, an impact mechanism subassembly, and a quick-change tool gripper subassembly. The rotary motion transformer subassembly includes a linear bushing connected to a drill bit, wherein the drill bit provides rotational motion, and the rotary motion transformer subassembly transforms the rotational motion into a reciprocal motion. The rotary motion further includes a crank bar for providing the reciprocal motion and the reciprocal motion is provided to the impact mechanism subassembly that includes wave springs for providing necessary forces to an impactor tool attached to the quick-change tool gripper subassembly. The impactor tool, upon receiving power from the impact mechanism subassembly, can provide a controlled impact to a selected bone or joint.

In yet another embodiment of the present invention, the impact mechanism subassembly includes a switch that is configured for adjusting the impact force applied by the device. The switch can be configured to adjust the tension provided by the wave spring for adjusting the impact force of the device. In yet another embodiment, the device can be electrically or battery powered by a built-in or a separate power source, for example, an 80-watt 24-volt rechargeable battery.

In yet another embodiment of the present invention, the rotary motion converting mechanism subassembly of the orthopedic impacting device includes bearings, retaining keys, dynamic seal, passive slant shaft, crank bar, linear bushing and an anvil that can be assembled by specifically designed assembly tools.

In yet another embodiment of the present invention, the adjustable impacting mechanism subassembly of the orthopedic impacting device includes SS wave springs and a secondary anvil that can be assembled by specifically designed assembly tools.

In yet another embodiment, a method for providing an accurate and precise impact on a bone or a joint of a patient by a surgeon during an orthopedic surgery or procedure is described. The method includes initially providing an orthopedic impacting device, then attaching a desired impactor to the impactor tool inlet of the device based on the type of bone or joint on which the impact is to be applied, then setting an impact level to be provided by the device based on the bone type wherein the setting is done by rotating the adjusting switch in a clockwise or counter-clockwise direction, thereafter attaching the attachment device to a medical drill using the drill bit wherein the medical drill provides the rotational force, and providing reciprocal force to the impactor tool by converting the rotational motion into linear or sliding motion.

In view of the foregoing disadvantages of the prior art, a medical drill orthopedic impact attachment configured to include all the advantages of the prior art and to overcome the drawbacks inherent therein is provided. The attachment can be used with any medical drill and by orthopedic surgeons for orthopedic impacting in various bones, joints and the like. The tool is capable of holding any impactor tool such as a broach, chisel or other end effector. Further, the switch for adjusting the impact power enables adjustment of the impact settings according to a particular bone type or other profile of a patient. The attachment advantageously augments the existing surgeon's skill in performing orthopedic procedures with accuracy and effectiveness.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and are intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which.

DETAILED DESCRIPTION OF THE PRESENT INVENTION

Figure 1:
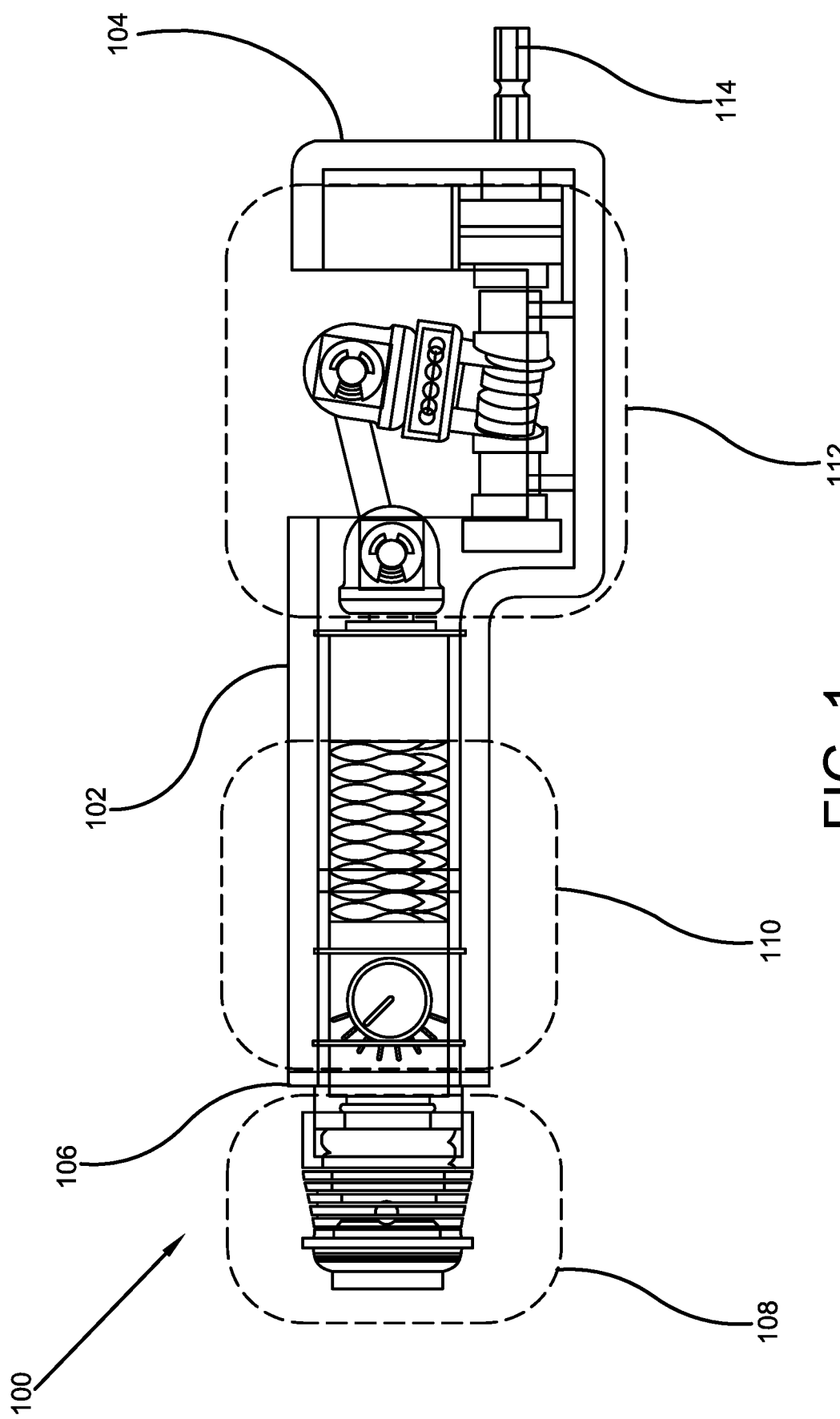
FIG. 1 illustrates a perspective view of one potential embodiment of the orthopedic surgery impact attachment of the present invention in accordance with the disclosed architecture.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof. Various embodiments are discussed hereinafter. It should be noted that the figures are described only to facilitate the description of the embodiments. They are not intended as an exhaustive description of the invention and do not limit the scope of the invention. Additionally, an illustrated embodiment need not have all the aspects or advantages shown. Thus, in other embodiments, any of the features described herein from different embodiments may be combined.

As noted above, there exists a long felt need in the art for an orthopedic surgery impact tool that enables orthopedic surgeries to be more accurate and reliable. There is also a long felt need in the art for an orthopedic surgery impact tool that can be easily used on any bone, disc, joint or more. Additionally, there is a long felt need in the art for an orthopedic surgery impact tool that eliminates the use of a manual hammer for creating an impact. Moreover, there is a long felt need in the art for an orthopedic surgery impact tool that enables users to adjust and control the frequency and energy of each impact. Furthermore, there is a long felt need in the art for an orthopedic surgery impact tool that is easy to carry and easy to use without tiring the surgeon. Finally, there is a long felt need in the art for an orthopedic surgery impact tool that improves the overall effectiveness of orthopedic surgeries and prevents further injury to the patient.

The present invention, in one exemplary embodiment, is a novel orthopedic surgery impact attachment is disclosed. The orthopedic surgery impact attachment includes a rotary motion transformer subassembly, an impact mechanism subassembly and a quick-change tool gripper subassembly. The rotary motion transformer subassembly includes a linear bushing connected to a drill bit wherein the drill bit provides rotational motion, and the rotary motion transformer subassembly transforms the rotational motion into a reciprocal motion. The rotary motion further includes a crank bar for providing the reciprocal motion and the reciprocal motion is provided to the impact mechanism subassembly that included wave springs for providing necessary force to an impactor tool attached to the quick-change tool gripper subassembly. A wave spring, also known as coiled wave spring, is a spring made up of pre-hardened flat wire in a process called on-edge coiling (also known as edge-winding). During this process, waves are added to give it a spring effect. The number of turns and waves can be easily adjusted to accommodate stronger force or meet specific requirements. A wave spring has advantages over a traditional coiled spring or a washer. Axial space can be reduced by up to 50%. As a result, the overall size of the assembly becomes smaller, reducing weight and production cost. The load in an axial direction is 100% transferable. One multi-turn wave spring can replace multiple stacked wave washers. This eases installation and reduces maintenance times. A wave spring can accommodate higher thrust load within the axial space as only the wire size, number of waves, wave height, and number of turns need to be adjusted to accommodate higher thrust loads. The impactor tool upon receiving power from the impact mechanism subassembly, provides an impact on a bone or joint.

Figure 3:
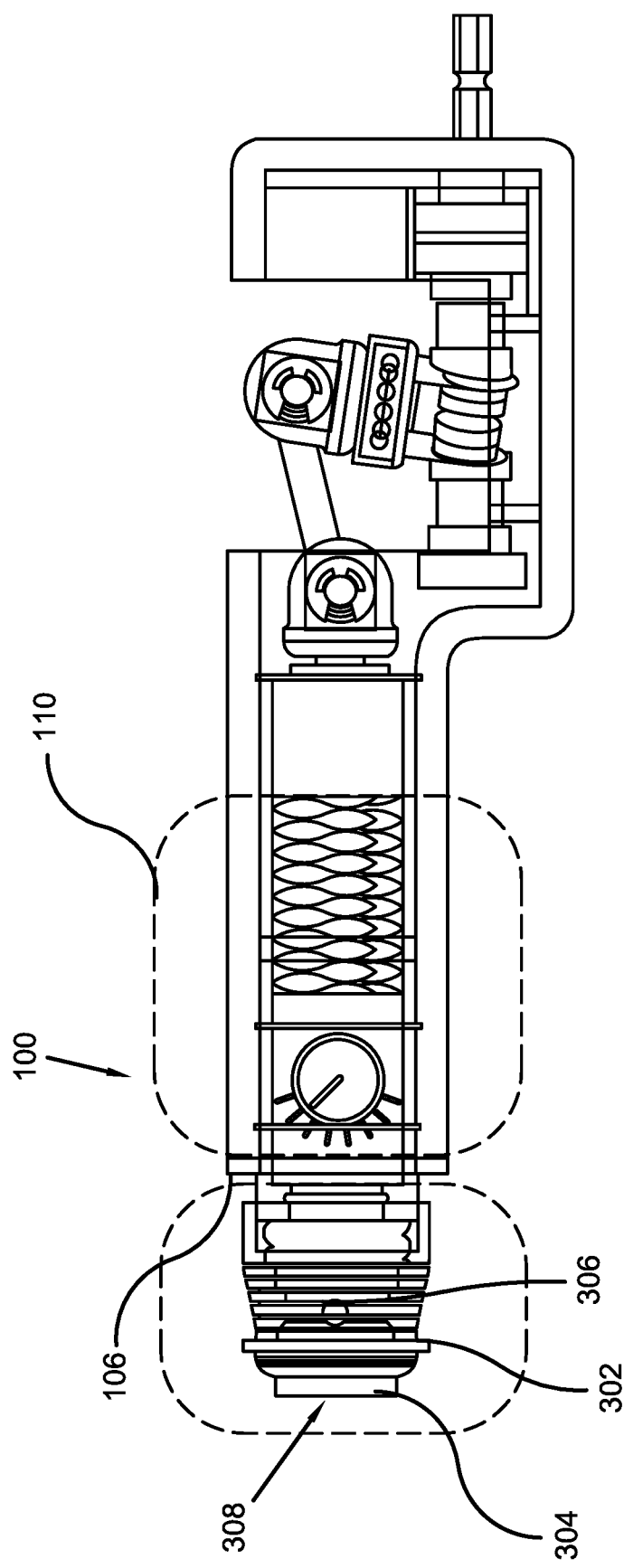
FIG. 3 illustrates a perspective view showing details of the attachment head at the distal end of one potential embodiment of the medical drill attachment device of the present invention in accordance with the disclosed architecture.

Referring initially to the drawings, FIG. 1 illustrates a perspective view of one potential embodiment of the orthopedic surgery impact attachment of the present invention in accordance with the disclosed architecture. The orthopedic surgery impact attachment 100 of the present invention is designed as an impact attachment for a medical drill for use in orthopedic surgeries and procedures. More specifically, the attachment 100 transforms the rotational motion of the drill to which the attachment 100 is attached into a reciprocal motion for creating impact forces that can be transferred onto a bone, disc, joint, etc. The attachment 100 is lightweight, portable and is configured to receive an impactor tool that creates an impact on a patient's bone or joint. The attachment 100 includes a housing 102 that securely covers and holds at least one subassembly of the attachment 100. The housing 102 includes a proximal end 104 and a distal end 106. The attachment 100 is secured to a medical drill using the drill attachment 114 positioned at the proximal end 104 of the housing 102. At the distal end 106 of the housing 102, a quick-change tool gripper assembly 108 is attached. The quick-change tool gripper assembly 108 includes an impact tool change gripper to which an impactor tool can be detachably-attached as best shown in FIG. 3.

The housing 102 includes a rotary motion converting mechanism subassembly 112 near to the proximal end 104 for transforming rotational motion of the medical drill into a reciprocal motion and an adjustable impacting mechanism subassembly 110 near the distal end 106 of the housing 102. The adjustable impacting mechanism 110 enables users to adjust and control the frequency and energy of each impact. All the components of both the rotary motion converting mechanism assembly 112 and the adjustable impacting mechanism 110 are housed within the housing 102 for a safe and secure operation. Details of the components of both the assemblies 110, 112 are described in FIG. 2. The subassemblies 110, 112 can be assembled inside the housing 102 and the housing 102 can be made from anodized aluminum.

Figure 2:
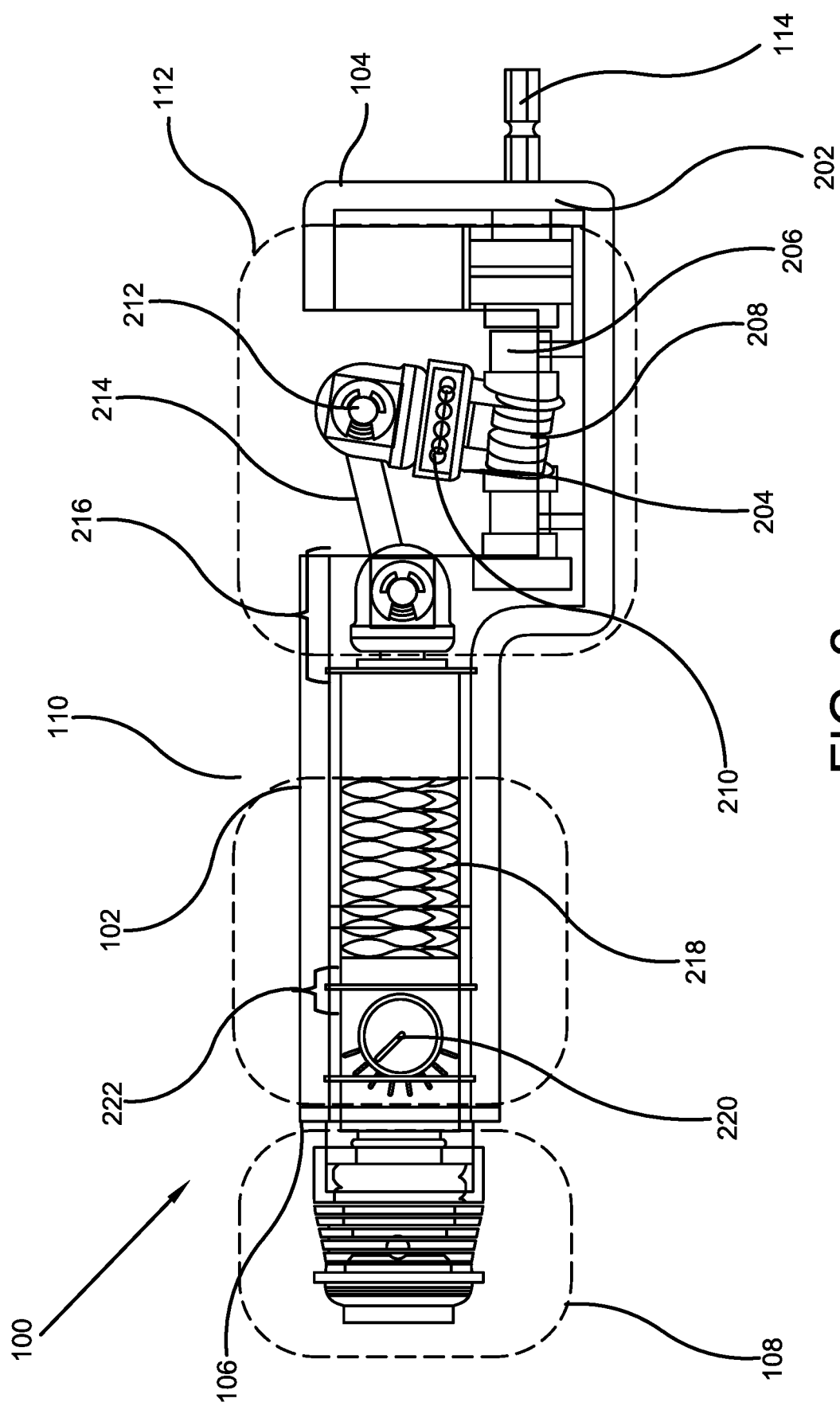
FIG. 2 illustrates an internal view of one potential embodiment of the orthopedic surgery impact attachment of the present invention showing components of the adjustable impacting mechanism subassembly and the rotary motion converting mechanism subassembly in accordance with the disclosed architecture.

FIG. 2 illustrates an internal view of the orthopedic surgery impact attachment of the present invention showing components of the adjustable impacting mechanism subassembly 110 and the rotary motion converting mechanism subassembly 112 in accordance with the disclosed architecture. The rotary motion converting mechanism subassembly 112 is connected to the drill bit 114 through the connector 202. The rotary motion converting mechanism subassembly 112 includes bearings 210, retaining keys 208, a dynamic seal (not shown), a passive slant shaft 214, a crank 212, a linear bushing 204 and a first anvil 216 that can be assembled by specifically designed assembly tools. In use, the drill 114 provides the rotational motion which in turn rotates the linear bushing 204. The linear bushing 204 is connected to the connector 202 through a linear motion (LM) shaft 206. A linear motion shaft (LM Shaft) can be a hardened and ground shaft featuring high precision for rectilinear motion which can be used in conjunction with a ball bushing. The linear bushing 204 is the linear motion component that is used in combination with the cylindrical LM shaft 206 and enables straight or linear motion with minimal frictional resistance and therefore smooth motion. A molded resin retainer 208 can be incorporated in order to prevent the ball bearings 210 from falling out. The retainer 208 also provides silent and smooth operation of the device. The linear bushing 204 can be connected to a crank 212 that is designed to slide a connected passive slant shaft 214. The passive slant shaft 214 can be attached to a first anvil 216 that slides forward and backward to provide a sliding mechanism. The crank 212 converts the rotation motion into the sliding motion of the first anvil 216. It should be noted that a seal used for linear bushing 204 keeps contamination out and maintains lubrication to ensure that the linear bushing 204 operates properly without premature wear or failure. The seal present in the linear bushing 204 is the internal seal which is also referred to as the universal seal. The crank 212 functions as a small rotating disc whose rotation drives the sliding or the linear motion of the first anvil 216. The passive slant shaft 214 acts as the rod for the crank system and slides the first anvil 216 in forward and backward directions.

The first anvil 216, when slid towards the distal end 106 of the housing 102, pushes the stainless-steel wave spring 218. The wave spring 218 is a functional part of the adjustable impacting mechanism subassembly 110. The wave spring 218 can be preferably made from coiled flat stainless-steel wire with waves added to give it a spring effect. The wave spring 218 occupies less space than conventional torsional springs, and uses less materials, hence lower production costs. Advantageously, the bending load in the waves provides one hundred percent axial transmission towards the distal end 106 of the housing 102. Near the distal end 106 of the housing 102, a switch 220 is disposed that adjusts the impact power of the device 100 being applied to the patient's body part. The switch 220 can be configured to rotate in both clockwise and counter-clockwise directions, and accordingly can increase or decrease the impact power, respectively. More specifically, the switch 220 modifies the compression rate of the wave spring 218 that enables the impact power to adjust. For example, if the switch 220 is rotated in a clockwise direction, the tension in the wave spring 218 increases and thus a higher impact is exerted by the attachment on a patient. This adjustment of the pressure is important as it makes the attachment device 100 of the present invention compatible and useful for all types of orthopedic surgeries and procedures. The wave spring 218 is attached to a secondary anvil 222 for a connection with the quick-change tool gripper assembly 108.

FIG. 3 illustrates a perspective view showing details of the attachment head at the distal end 106 of the medical drill attachment device 100 of the present invention in accordance with the disclosed architecture. At the distal end 106, the quick-change tool gripper 302 is attached via a central shaft 306. The shaft 306 also connects to the adjustable impacting mechanism subassembly 110. At the front end 304 of the quick-change tool gripper 302, an impactor tool inlet 308 is present that is configured to receive an impactor tool such as a broach, chisel or any other impactor for providing an impact on a bone, joint or the like. Based on the type of the bone, the impactor can be changed for providing an accurate and effective drill and orthopedic procedure. The quick-change tool gripper 302 can be made up of rubber or silicon and receives the impactor such that a linear motion to the impactor is provided by the adjustable impacting mechanism subassembly 110.

Figure 4:
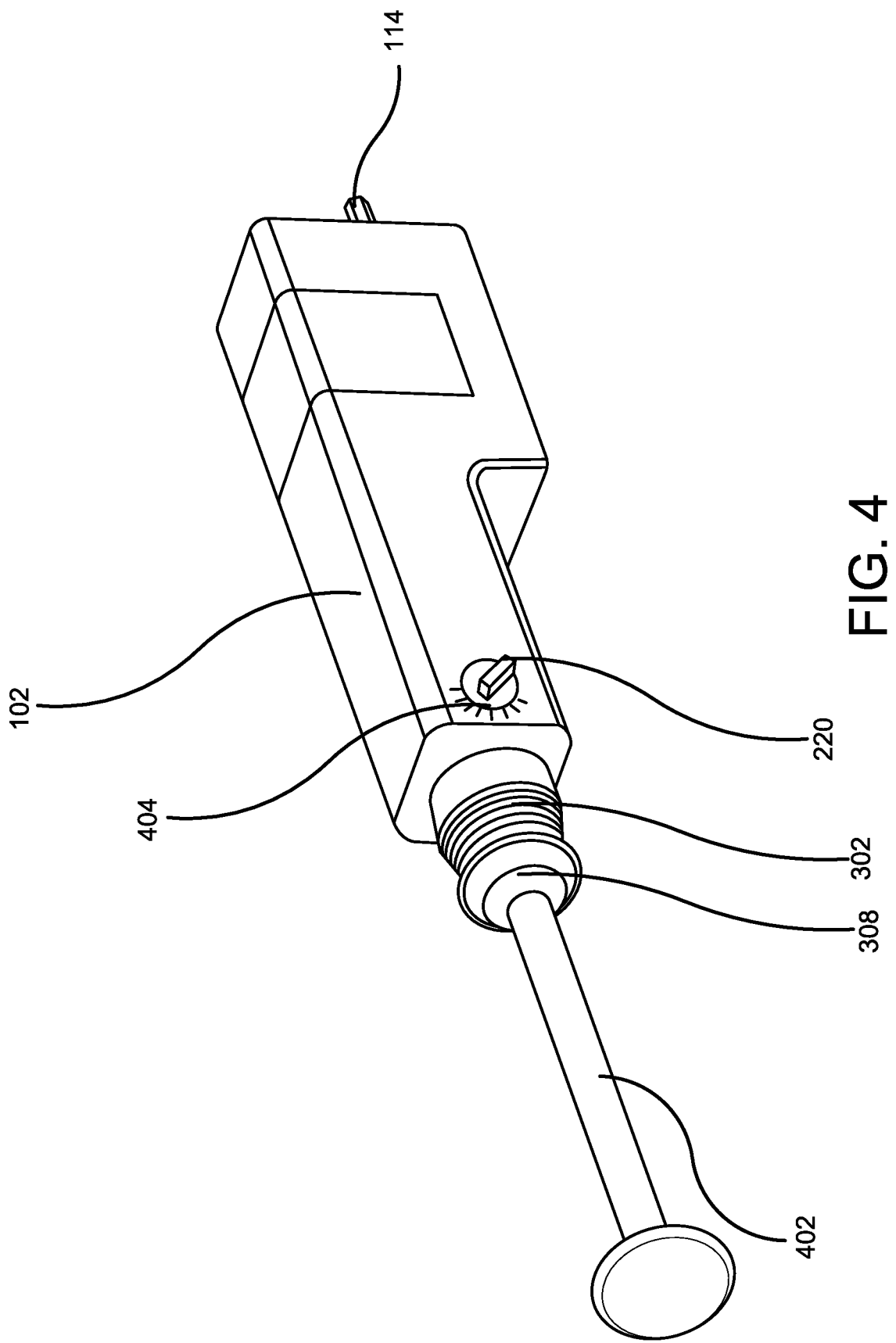
FIG. 4 illustrates a perspective view of one potential embodiment of the medical drill attachment device of the present invention showing an impactor tool attached to the quick-change tool gripper in accordance with the disclosed architecture.

FIG. 4 illustrates a perspective view of the medical drill attachment device 100 of the present invention showing an impactor tool 402 attached to the quick-change tool gripper 302 in accordance with the disclosed architecture. For performing drilling and other orthopedic procedures, a selectable or desired impactor tool 402 can be detachably-attached to the impactor tool inlet 308 such that rotational motion provided by the drill bit 114 being converted to the transitional motion by the device 100 is provided to the impactor tool 402 for providing the impact on a bone, joint or the like, of a patient. The desired impactor tool 402 can be replaced with another tool based on the type of the bone or joint. For example, a broach or a chisel can be replaced with different types of other impactors allowing the surgeons to use a single device for performing various types of orthopedic surgeries and procedures. Further, after attaching the desired impactor tool 402, the switch 220 can be used for adjusting the impact provided by the device 100. The switch 220 includes a plurality of markers 404 on the body of the housing 102 wherein the markers 404 are used for setting a particular desired level of the impact that can be provided by the desired impactor tool 402.

Figure 5:
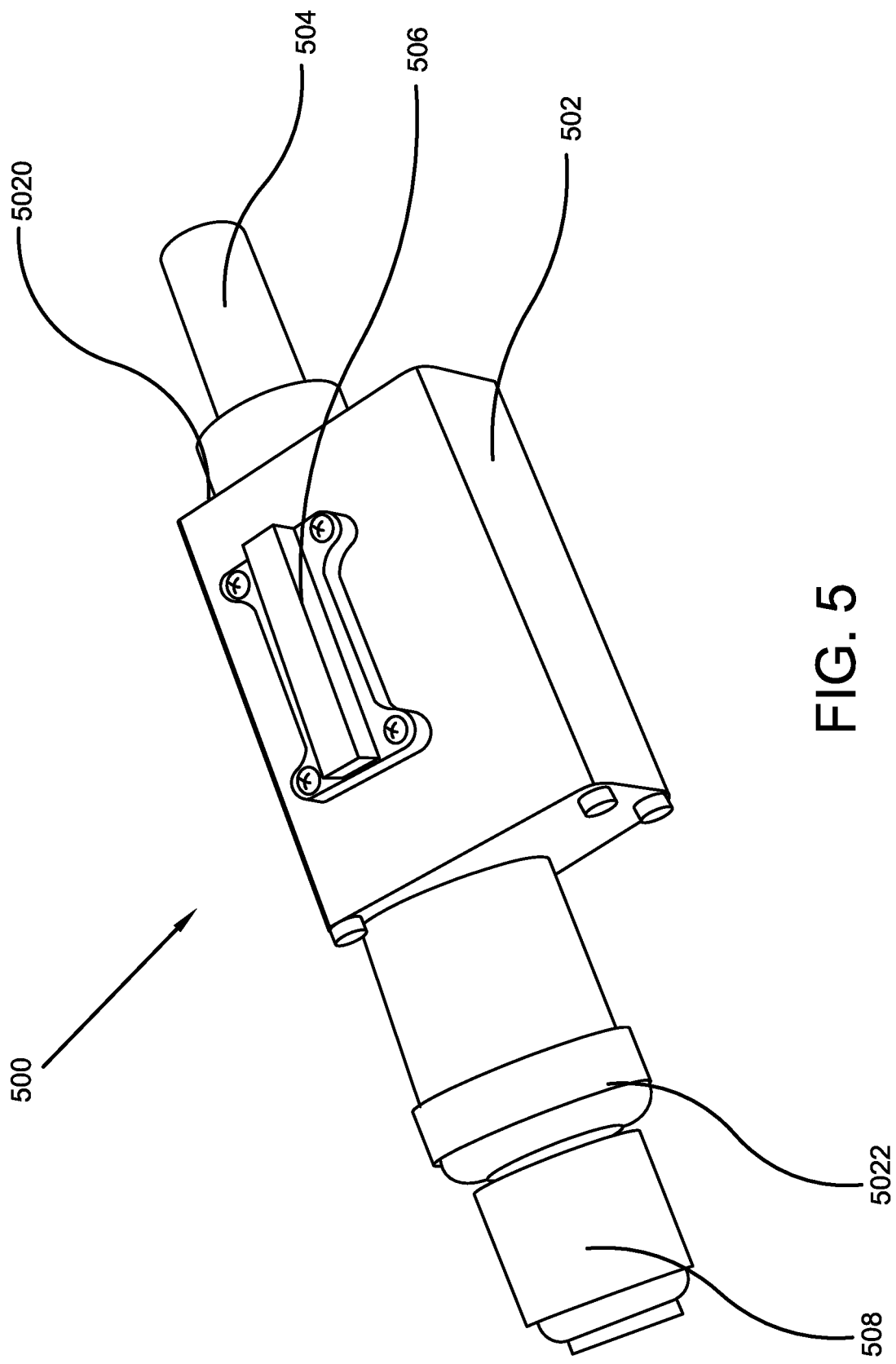
FIG. 5 illustrates a perspective view showing another potential embodiment of the medical drill attachment device of the present invention in accordance with the disclosed architecture.

FIG. 5 illustrates a perspective view showing another embodiment of the medical drill attachment device of the present invention in accordance with the disclosed architecture. The present embodiment shows the attachment device 500 that provides a fixed impact. The attachment device 500 includes the specifications similar to the device 100 of the other embodiments of the present invention, but without the presence of the adjustable switch. The device 500 includes a housing 502 that securely covers and includes all the necessary components of the device 500. Further, the housing 502 at a first end 5020 includes the drill bit 504 for securing to a medical drill and includes the impactor connector 508 at the second end 5022. The device 500 is provided with a battery 506 that is used for providing power to the device 500. The battery 506 can be 80-watt 24-volt rechargeable battery, or can be any other means for providing power to the device 500. It should be noted that all embodiments of the present invention can include a rechargeable battery, preferably an 80-watt 24-volt lithium ion (Li-Ion) battery.

Figure 6:
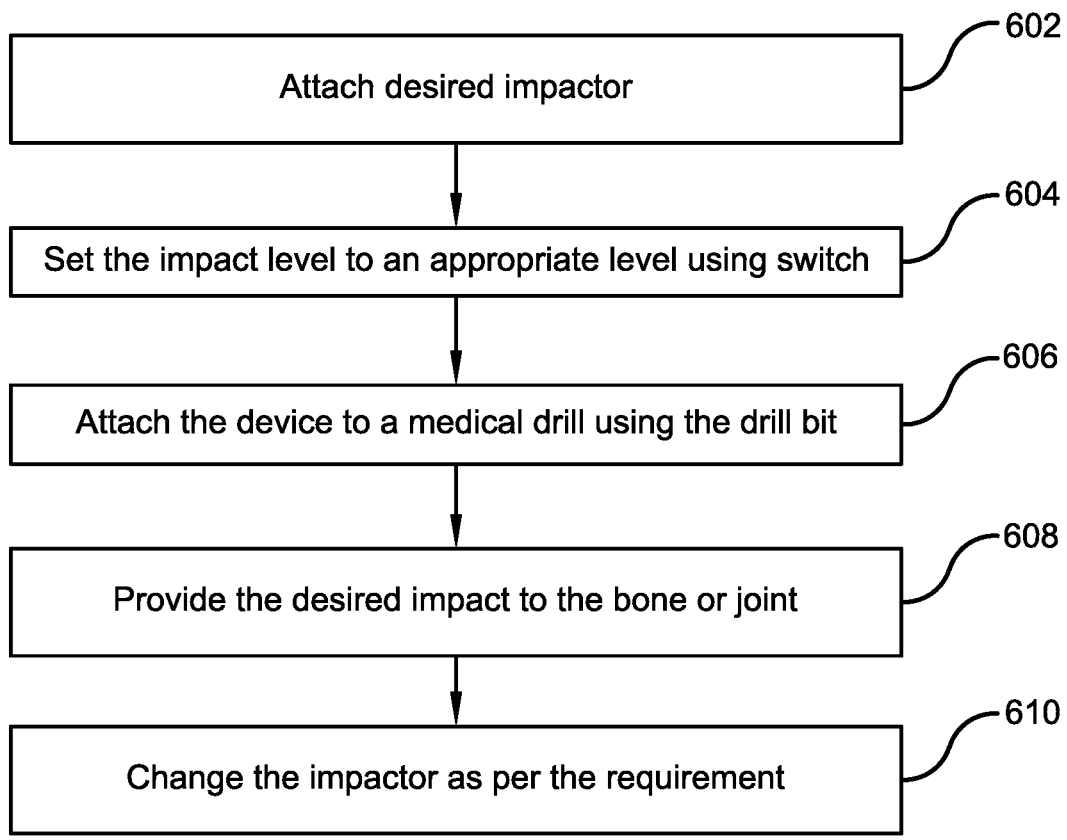
FIG. 6 illustrates a flow diagram showing exemplary steps performed by a surgeon for using one potential embodiment of the medical drill attachment device of the present invention in accordance with the disclosed architecture.

FIG. 6 illustrates a flow diagram showing exemplary steps performed by a surgeon for using the attachment device 100 of the present invention in accordance with the disclosed architecture. It should be understood that the present embodiment states the basic flow performed by a user and additional actions may be used to add additional processes to the basic flow. Initially, a desired impactor is attached to the impactor tool inlet of the device based on the type of bone and/or joint on which the impact is to be applied (Block 602). Then, an impact level can be set based on the bone type by rotating the adjusting switch in clockwise or counter-clockwise directions (Block 604). The aforementioned enables users to adjust and control the frequency and energy of each impact. Thereafter, the attachment device can be attached to a medical drill using the drill bit (Block 606) wherein the medical drill provides the rotational force. By converting the rotational motion into linear or sliding motion, an impact can be provided by the impactor tool in a precise and accurate manner (Block 608). Finally, the impactor tool can be removed and replaced with another impactor tool for any other type of bone or joint (Block 610).

Certain terms are used throughout the following description and claims to refer to particular features or components. As one skilled in the art will appreciate, different persons may refer to the same feature or component by different names. This document does not intend to distinguish between components or features that differ in name but not structure or function. As used herein "orthopedic surgery impact attachment", "attachment", "medical drill attachment device", "attachment device" and "device" are interchangeable and refer to the orthopedic surgery impact attachment 100 of the present invention.

Notwithstanding the forgoing, the orthopedic surgery impact attachment 100 of the present invention can be of any suitable size and configuration as is known in the art without affecting the overall concept of the invention, provided that it accomplishes the above-stated objectives. One of ordinary skill in the art will appreciate that the size, configuration and material of the orthopedic surgery impact attachment 100 as shown in the FIGS. are for illustrative purposes only, and that many other sizes and shapes of the orthopedic surgery impact attachment 100 are well within the scope of the present disclosure. Although the dimensions of the orthopedic surgery impact attachment 100 are important design parameters for user convenience, the orthopedic surgery impact attachment 100 may be of any size that ensures optimal performance during use and/or that suits the user's needs and/or preferences.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. An orthopedic impactor device comprising:
   a housing comprising a quick-change tool gripper mechanism at a distal end, a rotary motion converting mechanism at a proximal end, and an adjustable impacting mechanism therebetween;
   wherein said housing further comprises a drill attachment at said proximal end;
   wherein said rotary motion converting mechanism transforms a rotational motion into a reciprocal motion to said adjustable impacting mechanism;
   wherein said drill attachment is securable to a drill for providing said rotational motion;
   wherein said quick-change tool gripper mechanism comprises an impact tool change gripper to which a first impactor tool can be selectively attached;
   a switch disposed along said housing for varying an impact power of said adjustable impacting mechanism; and
   wherein said rotary motion converting mechanism comprises a linear motion shaft and a linear bushing for transmitting said rotational motion to a crank.

2. The orthopedic impactor device of claim 1, wherein said switch is rotatable in both a clockwise direction and a counter-clockwise direction for said varying of said impact power of said adjustable impacting mechanism.

3. The orthopedic impactor device of claim 2, wherein said varying of said impact power includes modifying a compression rate of a wave spring in said adjustable impacting mechanism.

4. The orthopedic impactor device of claim 3, wherein said wave spring comprises a coiled flat stainless-steel wire.

5. The orthopedic impactor device of claim 2, wherein said varying of said impact power includes adjusting a tension of a wave spring in said adjustable impacting mechanism.

6. The orthopedic impactor device of claim 2, wherein said varying of said impact power includes modifying a frequency rate of said adjustable impacting mechanism.

7. The orthopedic impactor device of claim 6, wherein said housing is comprised of an anodized aluminum.

8. The orthopedic impactor device of claim 1, wherein said crank reciprocates a shaft for actuating a first anvil and a second anvil.

9. The orthopedic impactor device of claim 8, wherein said first anvil slides linearly forward and backward in said housing.

10. The orthopedic impactor device of claim 9, further comprising at least a second impactor tool for selective attachment to said quick-change tool gripper mechanism.

11. An orthopedic impactor device comprising:
    a housing comprising a quick-change tool gripper mechanism at a distal end, a rotary motion converting mechanism at a proximal end, and an adjustable impacting mechanism therebetween;
    wherein said rotary motion converting mechanism transforms a rotational motion into a reciprocal motion to said adjustable impacting mechanism;
    wherein said quick-change tool gripper mechanism includes an impact tool change gripper to which a first impactor tool can be selectively attached; and
    a switch disposed along said housing for varying an impact power of said adjustable impacting mechanism;
    wherein said switch is rotatable in both a clockwise direction and a counter-clockwise direction for said varying of said impact power of said adjustable impacting mechanism; and
    wherein said varying of said impact power includes modifying a compression rate of a wave spring in said adjustable impacting mechanism.

12. The orthopedic impactor device of claim 11, wherein said housing further comprises a drill attachment at said proximal end and said drill attachment is securable to a drill for providing said rotational motion.

13. The orthopedic impactor device of claim 12, wherein said housing is comprised of an anodized aluminum.

14. The orthopedic impactor device of claim 11, wherein said rotary motion converting mechanism comprises a linear motion shaft and a linear bushing for transmitting said rotational motion to a crank.

15. The orthopedic impactor device of claim 14, wherein said crank reciprocates a shaft for actuating a first anvil and a second anvil.

16. The orthopedic impactor device of claim 15, wherein said first anvil slides linearly forward and backward in said housing.

17. The orthopedic impactor device of claim 16, further comprising at least a second impactor tool for selective attachment to said quick-change tool gripper mechanism.

18. An orthopedic impactor device comprising:
    a housing comprising a quick-change tool gripper mechanism at a distal end, a rotary motion converting mechanism at a proximal end, and an adjustable impacting mechanism therebetween;
    wherein said rotary motion converting mechanism transforms a rotational motion into a reciprocal motion to said adjustable impacting mechanism;
    wherein said housing further comprises a drill attachment at said proximal end and said drill attachment is securable to a drill for providing said rotational motion;
    wherein said rotary motion converting mechanism includes a linear motion shaft and a linear bushing for transmitting said rotational motion to a crank;

wherein said crank reciprocates a shaft for actuating a first anvil and a second anvil;

wherein said first anvil slides linearly forward and backward in said housing; and wherein said quick-change tool gripper mechanism includes an impact tool change gripper to which a first impactor tool and at least a second impactor tool are selectively attached.

\* \* \* \* \*